United States Patent [19]

Le Count et al.

[11] Patent Number: 4,607,039

[45] Date of Patent: * Aug. 19, 1986

[54] QUINOLINE DERIVATIVES WHICH ARE 5-HYDROXYTRYPTAMINE ANTAGONISTS

[75] Inventors: David J. Le Count, Congleton; Robert J. Pearce, Wilmslow, both of United Kingdom

[73] Assignee: Imperial Chemical Industries PLC, London, England

[*] Notice: The portion of the term of this patent subsequent to Mar. 6, 2001 has been disclaimed.

[21] Appl. No.: 488,607

[22] Filed: Apr. 25, 1983

[30] Foreign Application Priority Data

May 4, 1982 [GB] United Kingdom ............... 8212787
Jan. 27, 1983 [GB] United Kingdom ............... 8302236

[51] Int. Cl.⁴ .................. A61K 31/47; C07D 215/36
[52] U.S. Cl. .......................... 514/312; 546/155; 546/157
[58] Field of Search ............ 546/155, 157; 424/258; 514/312

[56] References Cited

U.S. PATENT DOCUMENTS

| | | | |
|---|---|---|---|
| Re. 16,394 | 7/1926 | Callsen | 546/157 |
| 1,572,768 | 9/1926 | Callsen | 546/157 |
| 1,860,286 | 5/1932 | Hartmann | 546/157 X |
| 4,035,374 | 7/1977 | Durant et al. | 546/153 X |
| 4,235,909 | 11/1980 | Bach et al. | 546/153 X |
| 4,260,764 | 4/1981 | Johnson | 546/153 |
| 4,343,805 | 8/1982 | Crossley et al. | 424/258 X |
| 4,426,387 | 1/1984 | Archibald et al. | 546/153 X |
| 4,435,405 | 3/1984 | Blackburn et al. | 546/157 |

FOREIGN PATENT DOCUMENTS

| | | | |
|---|---|---|---|
| 0430960 | 7/1924 | Fed. Rep. of Germany | 546/157 |
| 0349761 | 6/1931 | United Kingdom | 546/157 |

OTHER PUBLICATIONS

Gilman, et al., J. Am. Chem. Soc., vol. 71, pp. 3667–3668 (1949).
Westland, et al., J. Med. Chem., vol. 16(4), pp. 319–327 (1973).
Zayed, et al., Pharmazie, vol. 33(9), pp. 572–575 (1978).
Soc. Anon. pour l'Ind. a Bale, Chemical Abstracts, vol. 26, 3624 (1932).
A. Wander A.-G., Chemical Abstracts, vol. 43, 7974e (1949).
Aryuzina, et al., Chemical Abstracts, vol. 60, 7990f (1964).
Pettit, et al., Chemical Abstracts, vol. 61, 8271f (1964).

Primary Examiner—Donald G. Daus
Assistant Examiner—Diana G. Rivers
Attorney, Agent, or Firm—Cushman, Darby & Cushman

[57] ABSTRACT

Compounds of the formula:

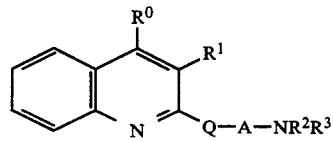

wherein A stands for the radical —(CH$_2$)$_2$— which may optionally be substituted by one or two (1–2C)alkyl radicals; Q stands for an oxygen or sulphur atom; R° stands for a (1–4C)alkyl, (1–4C)alkoxy or cyclopropyl radical; R$^1$ stands for a defined (3–4C)alkyl radical, a phenyl radical which may optionally bear a defined substituent, or a defined heteroaryl radical of 5 or 6 ring atoms; and R$^2$ and R$^3$ stand for hydrogen or a (1–2C)alkyl radical; and pharmaceutically-acceptable acid-addition salts thereof. Processes for the manufacture of said compounds. Pharmaceutical compositions comprising one of said compounds and a pharmaceutical diluent or carrier. The compounds are 5-hydroxytryptamine antagonists.

7 Claims, No Drawings

QUINOLINE DERIVATIVES WHICH ARE 5-HYDROXYTRYPTAMINE ANTAGONISTS

This invention relates to quinoline derivatives which are active as 5-hydroxytryptamine antagonists in warm-blooded animals.

The compound 2-(2-diethylaminoethoxy)-3-phenyl-quinoline is described in U.S. Pat. No. 1,860,286, and it is stated therein that it exhibits antipyretic activity. However, there is no reason for one of ordinary skill in the art to deduce from this that compounds of this type would be 5-hydroxytryptamine (5-HT) antagonists.

According to the invention there are provided quinoline derivatives of the formula:

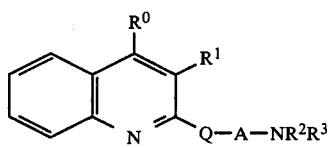

wherein:

A stands for the radical —(CH$_2$)$_2$—, which may optionally be substituted by one or two (1–2C)alkyl radicals;

Q stands for an oxygen or sulphur atom;

R$^o$ stands for a (1–4C)alkyl, (1–4C)alkoxy or cyclopropyl radical;

R$^1$ stands for an n-, iso- or s-(3–4C)alkyl radical, or a cyclopropyl radical, or it stands for a phenyl radical which may optionally be substituted with a halogen atom or a (1–2C)alkyl, (1–2C)alkoxy or (1–2C)perfluoroalkyl radical, or R$^1$ stands for a heteroaryl radical of five or six ring atoms containing one hetero-atom selected from oxygen, sulphur and nitrogen atoms; and R$^2$ and R$^3$, which may be the same or different, stand for hydrogen or a methyl or ethyl radical;

and pharmaceutically-acceptable acid-addition salts thereof.

Some of the compounds of the invention contain at least one asymmetric carbon atom; for example this is the case when A stands for the radical —(CH$_2$)$_2$— bearing a (1–2C)alkyl substituent. The racemic form of such compounds containing at least one asymmetric carbon atom can be resolved by conventional methods into the optically active isomers thereof. It is to be understood that the compounds of the invention consist of (a) the compounds of formula I in racemic form, and (b) the optical isomers thereof which are 5-HT antagonists.

A may, for example, stand for a 1,2-ethylene, 1,2-propylene, 2,3-propylene, 1,1-dimethyl-1,2-ethylene, or 2,2-dimethyl-1,2-ethylene radical.

R$^o$ may stand for a cyclopropyl radical, or a straight- or branched-chain (1–4C)alkyl or (1–4C)alkoxy radical, for example a methyl, ethyl, n-propyl, n-butyl, methoxy, ethoxy or n-propoxy radical.

R$^1$ may, for example, stand for an n-propyl, isopropyl, n-butyl, s-butyl or cyclopropyl radical. Alternatively, R$^1$ may, for example, stand for a phenyl radical which may optionally bear a substituent selected from fluorine, chlorine and bromine atoms, and (1–2C)alkyl radicals, for example a methyl radical, (1–2C)alkoxy radicals, for example a methoxy radical, and (1–2C)perfluoroalkyl radicals, for example a trifluoromethyl radical.

Alternatively, R$^1$ may stand for a heteroaryl radical of five or six ring atoms containing a single hetero-atom selected from oxygen, sulphur and nitrogen atoms, for example a furyl, thienyl or pyridyl radical.

According to one embodiment of the invention there are provided quinoline derivatives of the formula I wherein:

A stands for the radical —(CH$_2$)$_2$—, which may optionally bear one or two methyl substituents;

Q stands for an oxygen or sulphur atom;

R$^o$ stands for a (1–3C)alkyl or (1–3C)alkoxy radical;

R$^1$ stands for an n-propyl, isopropyl, phenyl, fluorophenyl, chlorophenyl, bromophenyl, tolyl, methoxyphenyl, trifluoromethylphenyl, thienyl or furyl radical; and R$^1$ and R$^2$, which may be the same or different, stand for hydrogen or a methyl radical;

and pharmaceutically-acceptable acid-addition salts thereof.

A group of preferred compounds of the invention consists of 2-(2-dimethylaminoethylthio)-4-methoxy-3-phenylquinoline, 2-(2-dimethylamino-2-methylpropylthio)-3-o-methoxyphenyl-4-methylquinoline, 2-(2-dimethylaminopropylthio)-4-methyl-3-phenylquinoline and 2-(2-dimethylamino-2-methylpropylthio)-3-isopropyl-4-methylquinoline, and pharmaceutically-acceptable acid-addition salts thereof. Particularly preferred compounds of the invention are 2-(2-dimethylamino-2-methylpropylthio)-4-methyl-3-phenylquinoline and pharmaceutically-acceptable acid-addition salts thereof.

Suitable salts of the invention are derived from inorganic or organic acids which provide a pharmaceutically-acceptable anion, for example hydrochloric, phosphoric, citric, benzoic, tartaric or succinic acid, or acids, for example 2-hydroxy-3-naphthoic acid or 1,1'-methylene-bis-2-hydroxy-3-naphthoic acid, which afford salts which are relatively insoluble in water and therefore have long-acting characteristics.

The compounds of the invention, and the compounds used as starting materials in the processes of the invention, may be obtained by processes which are known for the preparation of chemically analogous compounds. A compound containing at least one asymmetric carbon atom which is used as a starting material in a process of the invention may be used in a racemic or optically active form.

According to a further feature of the invention there is provided a process for the manufacture of the compounds of the formula I, wherein A, Q, R$^o$, R$^1$, R$^2$ and R$^3$ have the meanings stated above, and pharmaceutically-acceptable acid-addition salts thereof, which comprises reacting a compound of the formula:

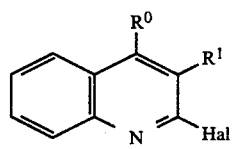

wherein

Hal stands for a halogen atom and R$^o$ and R$^1$ have the meanings stated above, with a compound of the formula:

wherein

A, Q, R² and R³ have the meanings stated above, or an acid-addition salt thereof, in the presence of an acid-binding agent.

Hal may, for example, stand for a chlorine or bromine atom. The salt of the compound of the formula III may, for example, be a salt derived from an inorganic acid, for example a hydrohalic acid, for example hydrochloric acid. The acid-binding agent may, for example, be sodium hydride. The reaction is conveniently carried out in a suitable organic solvent, for example dimethylformamide, and it may be accelerated or completed by the application of heat.

According to a further feature of the invention there is provided a process for the manufacture of the compounds of the formula I, wherein A, Q, $R^o$, $R^1$, $R^2$ and $R^3$ have the meanings stated above, and pharmaceutically-acceptable acid-addition salts thereof, which comprises reacting a compound of the formula:

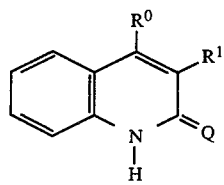
IV wherein
Q, $R^o$ and $R^1$ have the meanings stated above, with a compound of the formula:

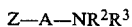
Z—A—NR²R³   V wherein
Z stands for a halogen atom or an arenesulphonyloxy or alkanesulphonyloxy radical, and A, R² and R³ have the meanings stated above, or an acid-addition salt thereof, in the presence of an acid-binding agent.

Z may, for example, stand for a chlorine or bromine atom or a p-toluenesulphonyloxy or methanesulphonyloxy radical. The salt of the compound of the formula V may, for example, be a salt derived from an inorganic acid, for example a hydrohalic acid, for example hydrochloric acid. The acid-binding agent may, for example, be sodium hydride. The reaction is conveniently carried out in a suitable organic solvent, for example dimethylformamide, and it may be carried out at ambient temperature or at an elevated temperature.

The activity of compounds of the invention as 5-HT antagonists has been demonstrated in the following tests:

(1) In vitro 5-HT receptor binding (a) Binding of tritiated 5-hydroxytryptamine ($[^3H]$5-HT)

This is an in vitro test of the affinity of test compounds for the central 5-HT₁ receptor (Molecular Pharmacology, 1979, 16, 687). The compounds are tested for their ability to displace $[^3H]$5-HT from a receptor site on a synaptosomal preparation prepared from rat brain tissue. The compounds are tested at 3 µg/ml., and they are declared active if they produce more than 30% inhibition of specific binding. Compounds of interest are tested at a range of concentrations to establish the absolute potency for this receptor. The results are expressed as pIC₅₀ values, the pIC₅₀ being the $-\log_{10}$ of the concentration of the compound needed to displace 50% of the specifically bound $[^3H]$5-HT.

(b) Binding of tritiated spiroperidol ($[^3H]$ spiroperidol)

This is an in vitro test of the affinity of test compounds for the central 5-HT₂ receptor (Molecular Pharmacology, 1979, 16, 687). The compounds are tested for their ability to displace $[^3H]$ spiroperidol from a receptor on a synaptosomal preparation prepared from rat brain cortex. The compounds are tested at 0.3 µg/ml., and they are declared active if they produce more than 30% inhibition of specific binding. Compounds of interest are tested at a range of concentrations as outlined above in respect of $[^3H]$5-HT binding. The results are expressed as pIC₅₀ values, the pIC₅₀ being the $-\log_{10}$ of the concentration of the compound needed to displace 50% of the specifically bound $[^3H]$ spiroperidol.

(2) Inhibition of head twitches induced in mice by 5-hydroxytryptophan (5-HTP)

This is an in vivo test of activity at central 5-HT receptors. The test involves administering a precursor of 5-HT, i.e. 5-HTP, to mice. The resultant high levels of 5-HT produced in the brain are believed to be responsible for the spontaneous twitching of the head and ears seen for a period after the administration of 5-HTP. All known centrally acting 5-HT antagonists inhibit the twitching response in a dose-dependent manner.

A range of doses of the compounds under test are administered intraperitoneally to male mice (average weight 18–20 g.; in groups of 5) 15 minutes before an intraperitoneal injection of 5-HTP at 300 mg./kg. The mice are then observed 15 minutes later for head twitches, and the results are expressed as ID₅₀ values. Non specific inhibition of the response due, for example, to sedation is eliminated by determining the presence of the pinna reflex to tactile stimulation of the ear.

(3) Antagonism of fenfluramine-induced hyperthermia in rats

This is a sensitive in vivo test which is based on the ability of fenfluramine to release 5-HT from endogenous neuronal stores.

Female rats (Alderley Park Strain; 180–220 g.) are housed (5 per cage) in a relatively warm environment (25°–28° C.) one hour prior to the beginning of the test to allow the animals to acclimatise. When the acclimatisation period is over, the rectal temperature of each animal is measured and these temperatures serve as the control reading from which all changes are calculated. For the recording of the control temperatures ($-1$ hour), either a test compound or the vehicle (distilled water) is administered orally or subcutaneously, and after a further hour (0 hour) the rectal temperature of each rat is measured. A dose of 15 mg./kg. of fenfluramine, or distilled water (controls), is then injected intraperitoneally. Rectal temperatures are then measured at the following times after the administration of the fenfluramine or distilled water:

30 minutes, and 1,2,3,4,5 and 6 hours

The potency of a compound in the test is expressed as an ID₅₀ value, i.e. the dose of the compound which reduces the hyperthermic response to a standard dose of fenfluramine by 50%.

The potency of a specific compound of the present invention depends upon its precise chemical structure, but generally speaking the compounds of the invention exhibit the following potencies in the following ranges in the above test:

Test (1)(a): $[^3H]$5-HT binding : pIC₅₀ 5–9

Test (1)(b): [$^3$H]spiroperidol binding : pIC$_{50}$ 5-9
Test (2) : ID$_{50}$ 0.1 to 50 mg./kg.
Test (3) : ID$_{50}$ 0.1 to 50 mg./kg.

No toxic effects or other undesirable effects have been observed with the compounds at doses at which they are active in the above-mentioned tests. Furthermore, as an indication of the lack of toxicity of a specific compound of the invention, namely 2-(2-dimethylamino-2-methylpropylthio)-4-methyl-3-phenylquinoline, that compound is tolerated in both the conscious dog and the marmoset at oral doses of up to 60 mg./kg.

Because of their activity as 5-HT antagonists the compounds of the invention may be used clinically in human patients as psychotropic agents for the treatment of diseases or dysfunctions of the central nervous system, for example psychoses, schizophrenia, mania, anxiety or depression, for the treatment of migraine, urticaria, asthma, hypertension, pulmonary hypertension, vascular spasm and gastrointestinal disorders, and for the inhibition of the aggregation of blood platelets. When one of the said compounds is used clinically in human patients it is recommended that it be dosed:

(a) orally at a dose of 0.5 mg./kg. to 100 mg./kg. at suitable intervals, for example three times per day, (b) intramuscularly at a dose of 0.1 mg./kg. to 20 mg./kg. at suitable intervals, (c) by means of a depot injection (2.5 to 100 mg./kg.), or (d) rectally at a dose of 0.5 mg./kg. to 200 mg./kg.

According to a further feature of the invention there are provided pharmaceutical compositions comprising a compound of the formula I wherein A, Q, R$^o$, R$^1$, R$^2$ and R$^3$ have the meanings stated above, or a pharmaceutically-acceptable acid-addition salt thereof, and an inert pharmaceutically-acceptable diluent or carrier.

The pharmaceutical compositions of the invention may be in a form suitable for oral, parenteral or rectal administration. Thus, for example, they may be in orally-administrable unit dosage form, for example tablets or capsules, which may optionally be adapted for sustained release, or in injectable form, for example a sterile injectable solution or suspension, or in the form of a suppository for rectal administration. The said pharmaceutical compositions may be produced by conventional methods using conventional diluents and carriers.

The pharmaceutical compositions of the invention may contain, in addition to a compound of the formula I, wherein A, Q, R$^o$, R$^1$, R$^2$ and R$^3$ have the meanings stated above, or a pharmaceutically-acceptable acid-addition salt thereof, one or more of the following medicaments:

1. known psychotropic agents, for example antipsychotic agents, for example chlorpromazine, haloperidol or fluphenazine, or anti-depressants, for example imipramine, mianserine or desmethylamitryptaline;

2. known anti-migraine agents, for example ergot alkaloids and derivatives thereof, and propranolol, clonidine, pitzotifen, O-acetylsalicylic acid or paracetamol;

3. known antihypertensive agents, for example α-methyldopa, α-adrenergic blocking agents, for example prazosin, β-adrenergic blocking agents, for example propranolol or atenolol, diuretics, for example hydrochlorothiazide, or frusemide, and vasodilators, for example minoxidil or hydrallazine; and 4. known platelet aggregation inhibitors, for example dipyridamol, anturan, sulphinpyrazone, ticlopidine or O-acetylsalicylic acid.

The invention is illustrated but not limited by the following Examples in which the temperatures are expressed in degrees Celsius:

EXAMPLE 1

Sodium hydride (0.25 g. of a 50% w/w dispersion in mineral oil) was added to a solution of 4-methoxy-3-o-tolylquinolin-2-thione (0.7 g.) in dimethylformamide (10 ml.) at ambient temperature. When all the hydrogen had evolved, 2-dimethylaminoethyl chloride hydrochloride (0.36 g.) was added and the mixture was stirred at ambient temperature for 20 hr. The reaction mixture was then poured into water (100 ml.) and extracted with ethyl acetate (2×25 ml.). The ethyl acetate extract was washed with water (2×10 ml.) and then dried (MgSO$_4$). The ethyl acetate was evaporated, the residue was dissolved in diethyl ether (50 ml.), and ethereal hydrogen chloride was added until precipitation was complete. The mixture was filtered and the solid residue was crystallised from ethanoldiethyl ether to give 2-(2-dimethylaminoethylthio)-4-methoxy-3-o-tolylquinoline hydrochloride, m.p. 196°-8°.

The 4-methoxy-3-o-tolylquinolin-2-thione used as starting material was prepared as follows:

A mixture of o-tolylacetic acid (10 g.), oxalyl chloride (10 ml.) and dimethylformamide (2 drops) was stirred at ambient temperature for 16 hr. The excess oxalyl chloride was evaporated, and the residue was dissolved in methylene dichloride (25 ml.) and added dropwise to a stirred ice-cold solution of methyl anthranilate (10 g.) and triethylamine (6.8 g.) in methylene dichloride (50 ml.). The mixture was stirred at ambient temperature for 20 hr. and then washed successively with 2M-hydrochloride acid (20 ml.), water (20 ml.), saturated sodium carbonate solution (20 ml.) and water (20 ml.), and then dried (MgSO$_4$). The methylene dichloride was evaporated and the residue was crystallised from ethyl acetate-petroleum ether (b.p. 60°-80°) to give methyl N-(o-tolylacetyl)anthranilate, m.p. 80°-2°.

A mixture of methyl N-(o-tolylacetyl)anthranilate (2.8 g.) and sodium hydride (1.1 g. of a 50% w/w dispersion in mineral oil) in toluene (50ml.) was heated at 100° for 1 hr. The reaction mixture was cooled and extracted with water (2×50 ml.). The aqueous extract was acidified to pH 2. The solid which precipitated was filtered off, stirred together with hot ethanol (25 ml.), and the mixture filtered to give 4-hydroxy-3-o-tolylquinolin-2-one, m.p. over 300°.

A mixture of 4-hydroxy-3-o-tolylquinolin-2-one (3 g.) and phosphorus oxychloride (15 ml.) was heated under reflux for 4 hr. and then stirred at ambient temperature for 20 hr. The mixture was poured into water (400 ml.) and extracted with diethyl ether (2×100 ml.). The ethereal extract was washed successively with saturated sodium bicarbonate solution (2×50 ml.) and water (2×50 ml.), and then dried (MgSO$_4$). The solvent was evaporated and the residue crystallised from methanol, to give 2,4-dichloro-3-o-tolylquinoline, m.p. 78°-80°.

A mixture of 2,4-dichloro-3-o-tolylquinoline (3 g.) and sodium methoxide (1.9 g.) in dimethylformamide (30 ml.) was heated at 60° for 6 hr. The mixture was cooled and poured into water (500 ml.), and the mixture was extracted with ethyl acetate (2×100 ml.). The ethyl acetate extract was washed with water (2×50 ml.) and then dried (MgSO$_4$). The solvent was evaporated and the residue (containing 2,4-dimethoxy-3-o-tolylquinoline) was used without further purification. A mixture of said residue (2.6 g.) and 2M-hydrochloric acid (50 ml.) was heated at 100° for 2 hr. The mixture was cooled and filtered. The solid residue was crystallised from ethyl acetate-petroleum ether (b.p. 60°-80°) to give 4-methoxy-3-o-tolylquinolin-2-one, m.p. 215°.

A mixture of 4-methoxy-3-o-tolylquinolin-2-one (1 g.) and 2,4-bis-(4-methoxyphenyl)-1,3-dithia-2,4-diphosphatane-2,4-disulphide (Lawesson's Reagent; 0.76 g.) in toluene (50 ml.) was heated under reflux for 1.5 hr. The mixture was then cooled and filtered; the solid residue was 4-methoxy-3-o-tolylquinolin-2-thione, m.p. 208°-210°.

EXAMPLE 2

The method described in the first paragraph of Example 1 was repeated except that the 4-methoxy-3-o-tolylquinolin-2-thione was replaced by an equivalent amount of 4-methoxy-3-phenylquinolin-2-thione. There was thus obtained 2-(2-dimethylaminoethylthio)-4-methoxy-3-phenylquinoline hydrochloride, m.p. 184°-7°.

The 4-methoxy-3-phenylquinolin-2-thione used as starting material (m.p. 221°-4°) was prepared from 4-methoxy-3-phenylquinolin-2-one in an analogous manner to that described in Example 1 for the preparation of 4-methoxy-3-o-tolylquinolin-2-thione.

EXAMPLE 3

4-Methyl-3-phenylquinolin-2-thione (5 g.) was added to a suspension of sodium hydride (2 g. of a 50% w/w dispersion in mineral oil, pre-washed with anhydrous toluene) in dimethylformamide (100 ml.) at ambient temperature. When the evolution of hydrogen had ceased, 2-dimethylamino-2-methylpropyl chloride hydrochloride (3.5 g.) was added, and the mixture was stirred at ambient temperature for 4 hr. The mixture was then poured into water (500 ml.) and extracted with ethyl acetate (3×200 ml.). The ethyl acetate extract was washed with water (2×100 ml.) and then dried (MgSO4). The ethyl acetate was evaporated in vacuo and the residue was chromatographed on silica gel (500 g.; Merck Kieselgel 60, Art 9385, grain size 0.040-0.063 mm., 230-400 mesh ASTM) using ethyl acetate: methanol 4:1 v/v as eluant. The appropriate fractions were combined and the solvents evaporated in vacuo. The oily residue (5.7 g.) was dissolved in methanol (50 ml.), and a solution of fumaric acid (3.8 g.) in methanol (50 ml.) was added. The resulting solution was evaporated in vacuo and the residue was crystallised from isopropanol to give 2-(2-dimethylamino-2-methylpropylthio)-4-methyl-3-phenylquinoline difumarate, m.p. 204°-5°.

The 4-methyl-3-phenylquinolin-2-thione used as starting material was prepared as follows:

A mixture of o-aminoacetophenone (25 g.) and phenylacetic acid (25 g.) in anhydrous methylene dichloride (200 ml.) was prepared. To that mixture was added dicyclohexylcarbodiimide (40 g.) in portions of approx. 10 g. every 5 min. at ambient temperature. When the addition was completed the mixture was stirred for 4 hr. at ambient temperature. The mixture was then filtered, and the filtrate was evaporated in vacuo to dryness. The residue was crystallised from cyclohexane to give o-acetyl-N-(phenylacetyl)aniline, m.p. 78°.

The aniline derivative (25 g.) was added to a solution of sodium hydroxide (1.5 g.) in water (150 ml.) and ethanol (50 ml.), and the mixture was heated under reflux for 5 hr. The resulting solution was cooled and acidified with concentrated hydrochloric acid to a pH of 2. The resulting mixture was filtered to give, as the solid residue, 4-methyl-3-phenylquinolin-2-one of m.p. 266°-8°. Using an analogous method to that described in Example 1 for the preparation of 4-methoxy-3-o-tolylquinolin-2-thione, the 4-methyl-3-phenylquinolin-2-one was converted into 4-methyl-3-phenylquinolin-2-thione, m.p. 265°-7°.

EXAMPLES 4-22

In an analogous manner to that described in Example 3, and using equivalent amounts of the appropriate quinolin-2-thione derivative and aminoalkyl chloride hydrochloride, the following compounds were obtained:

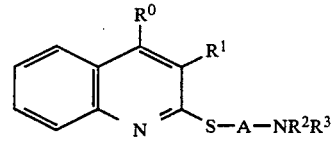

| Example | A | $R^0$ | $R^1$ | $R^2$ | $R^3$ | salt | m.p. | Crystallisation solvent |
|---|---|---|---|---|---|---|---|---|
| 4 | CH2CMe2 | Me | o-MeOPh | Me | Me | oxalate | 191-3 | Pr$^i$OH |
| 5 | CH2CMe2 | MeO | Ph | Me | Me | oxalate | 201-3 | MeOH |
| 6 | (CH2)2 | MeO | 3-thienyl | Me | Me | oxalate | 178-81 | EtOH |
| 7 | CH2CMe2 | MeO | 3-thienyl | Me | Me | oxalate | 171-3 | Pr$^i$OH |
| 8 | (CH2)2 | Pr$^n$O | Ph | Me | Me | oxalate | 211-3 | MeOH |
| 9 | CH2CMe2 | Pr$^n$O | Ph | Me | Me | oxalate | 125-6 | MeO(CH2)2—OMe/Et2O |
| 10 | (CH2)2 | Me | Ph | Me | Me | oxalate | 216-8 | MeCN |
| 11 | CH2CMe2 | Me | p-FPh | Me | Me | oxalate | 189-91 | EtOH |
| 12 | (CH2)2 | Me | o-MeOPh | Me | Me | oxalate | 183-5 | MeO(CH2)2—OMe/Et2O |
| 13 | CH2CMe2 | Me | 3-thienyl | Me | Me | oxalate | 185 | EtOH |
| 14 | (CH2)2 | Me | 3-thienyl | Me | Me | oxalate | 176-8 | Pr$^i$OH |
| 15 | (CH2)2 | Me | p-FPh | Me | Me | oxalate | 217-20 | EtOH |
| 16 | CH2CHMe | Me | Ph | Me | Me | fumarate | 174 | MeOH/Et2O |
| 17 | CH2CMe2 | Me | p-ClPh | Me | Me | (free base) | 127-8 | MeCN |
| 18 | CH2CMe2 | Me | p-CF3Ph | Me | Me | (free base) | 142-4 | MeCN |
| 19 | (CH2)2 | MeO | Ph | H | Me | oxalate | 207-9 | MeOH |
| 20 | (CH2)2 | MeO | Ph | H | H | oxalate | 169-71 | Pr$^i$OH |
| 21 | CH2CMe2 | Pr$^n$ | Ph | Me | Me | oxalate | 156-7 | Pr$^i$OH |

-continued

| Example | A | $R^o$ | $R^1$ | $R^2$ | $R^3$ | salt | m.p. | Crystallisation solvent |
|---|---|---|---|---|---|---|---|---|
| 22 | $CH_2CMe_2$ | Me | $Pr^i$ | Me | Me | oxalate | 148–50 | $Pr^iOH$ |

The following abbreviations are used in this Table:
Me methyl
$Pr^i$ isopropyl
Et ethyl
Ph phenyl
$Pr^n$ n-propyl The group A is shown in the Table in such a way that the sulphur atom is notionally to the left; thus, for example, Example 4 is a 2-dimethylamino-2-methylpropylthio derivative.

The following novel quinolin-2-thione derivatives (used as starting materials in the preparation of some of the above-mentioned compounds), and novel intermediates therefor, were prepared in an analogous manner to that described in Example 3:

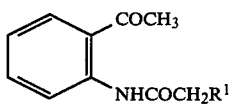

| Relevant Example(s) | $R^1$ | m.p. | Crystallisation solvent |
|---|---|---|---|
| 11,15 | p-FPh | 105–7 | cyclohexane |
| 13,14 | 3-thienyl | 70–3 | cyclohexane |
| 17 | p-ClPh | 79–80 | cyclohexane |
| 18 | p-$CF_3$Ph | 116–7 | cyclohexane |

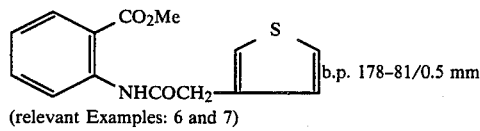

(relevant Examples: 6 and 7)

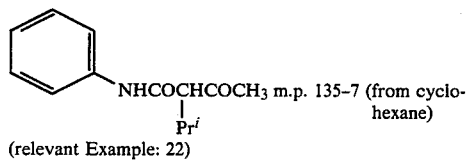

(relevant Example: 22)

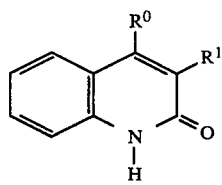

| Relevant Example(s) | $R^o$ | $R^1$ | m.p. | Crystallisation solvent |
|---|---|---|---|---|
| 11,15 | Me | p-FPh | 289–91 | dioxan |
| 13,14 | Me | 3-thienyl | 238–9 | (stirred with hot ethanol) |
| 17 | Me | p-ClPh | 275–7 | — |
| 18 | Me | p-$CF_3$Ph | 285–6 | — |
| 6,7 | MeO | 3-thienyl | 205–9 | — |
| 8,9 | $Pr^nO$ | Ph | 185–9 | — |

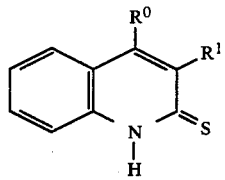

| Relevant Example(s) | $R^o$ | $R^1$ | m.p. |
|---|---|---|---|
| 11,15 | Me | p-FPh | 277–80 |
| 13,14 | Me | 3-thienyl | 278–80 |
| 17 | Me | p-ClPh | 286–8 |
| 18 | Me | p-$CF_3$Ph | 285–7 |
| 6,7 | MeO | 3-thienyl | 217–20 |
| 8,9 | $Pr^nO$ | Ph | 222–3 |

3-Isopropyl-4-methylquinolin-2-thione, which was used as a starting material in the preparation of Example 22, was obtained as follows:

Sodium hydride (0.48 g. of a 50% w/w dispersion in mineral oil) was added to a solution of 2-acetylacetanilide (1.8 g.) in dry dimethylformamide (15 ml.) under an atmosphere of argon. The mixture was stirred at 35° until the evolution of hydrogen had ceased. 2-Bromopropane (1.12 ml.) was added, and the mixture was heated at 55°–60° for 110 hr. The mixture was cooled and then poured into water (100 ml.). The resulting solution was adjusted to pH 2 with 3N-hydrochloric acid and extracted with ethyl acetate (3×100 ml.). The ethyl acetate extract was dried ($Na_2SO_4$) and the ethyl acetate was evaporated in vacuo. The residual oil was chromatographed on silica gel (Kieselgel 60, 180 g.) using 20% v/v ethyl acetate in petroleum ether (b.p. 60°–80°) as eluant. The relevant fraction was evaporated in vacuo, and the residue was crystallised from cyclohexane to give 2-acetyl-2-isopropylacetanilide, m.p. 135°–7°.

The last-named compound (2 g.) was stirred in 74% v/v sulphuric acid (25 ml.) at 95°–100° for 1 hr. The mixture was cooled and poured into water (200 ml.). The resulting mixture was filtered, and the solid residue was washed with hot isopropanol. There was thus obtained 3-isopropyl-4-methylquinolin-2-one, m.p. 247°–50°.

The said quinolone derivative (0.45 g.), together with Lawesson's Reagent (see Example 1; 0.45 g.) and dry toluene (10 ml.), was heated at 95°–100° for 2 hr. under an atmosphere of argon. The mixture was cooled and filtered, and the solid residue was washed with hot toluene. There was thus obtained 3-isopropyl-4-methylquinolin-2-thione, m.p. 226°–8°.

EXAMPLE 23

2-Dimethylamino-2-methylpropanol (0.74 g.) was added dropwise to a stirred suspension of sodium hydride (0.304 g. of a 50% w/w dispersion in mineral oil) in dry dimethylformamide (14 ml.), and when the addition was complete the mixture was stirred and heated at 40° for 1.5 hr. The mixture was cooled to ambient temperature, 2-chloro-4-methyl-3-phenylquinoline (1.6 g.) was added, and the mixture was stirred at 70° for 45 min. The mixture was cooled to ambient temperature, poured into water (70 ml.), and extracted with ethyl acetate (4×30 ml.). The ethyl acetate extract was washed with saturated brine (2×20 ml.), dried (Na$_2$SO$_4$), and evaporated in vacuo to dryness. The residue was chromatographed on silica gel (Kieselgel 60, 180 g.) using 0.5% v/v ammonium hydroxide/3% v/v methanol in ethyl acetate as the eluant. The relevant fraction was evaporated in vacuo to dryness. The residue (1.5 g.) was dissolved in isopropanol (10 ml.), and a solution of oxalic acid (0.40 g.) in isopropanol (10 ml.) was added. The resulting mixture was filtered, and the solid residue was crystallised from 1,2-dimethoxyethane. There was thus obtained 2-(2-dimethylamino-2-methylpropoxy)-4-methyl-3-phenylquinoline hydrogen oxalate, m.p. 105°–6°.

The quinoline derivative used as starting material was obtained as follows:

A mixture of 4-methyl-3-phenylquinolin-2-one (1.18 g.) and phosphorus oxychloride (60 ml.) was heated under reflux for 2 hr. The mixture was cooled and poured into ice-water (200 ml.), and the resulting mixture was extracted with ethyl acetate (3×50 ml.). The ethyl acetate extract was washed successively with saturated sodium carbonate solution (3×50 ml.) and water (50 ml.), dried (Na$_2$SO$_4$), and evaporated in vacuo to dryness. The residue was crystallised from cyclohexane to give 2-chloro-4-methyl-3-phenylquinoline, m.p. 88°–90°.

EXAMPLE 24

In an analogous manner to that described in Example 23, but using an equivalent amount of 2-dimethylaminoethanol in place of the 2-dimethylamino-2-methylpropanol, there was thus obtained 2-(2-dimethylaminoethoxy)-4-methyl-3-phenylquinoline hydrogen oxalate, m.p. 194°–6°.

What we claim is:
1. A compound of the formula:

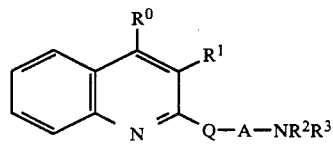

wherein:
A stands for —(CH$_2$)$_2$—, or —(CH$_2$)$_2$—which is substituted by not more than two (1–2C) alkyls;
Q stands for a sulphur atom;
R° stands for (1–4C)alkyl, (1–4C)alkoxy or cyclopropyl;
R$^1$ stands for a radical selected from the group consisting of n-, iso- or s-(3–4C)alkyl, cyclo-propyl, phenyl, halogenophenyl, (1–2C)alkyl-phenyl, (1–2C)alkoxy-phenyl or (1–2C)perfluoroalkyl-phenyl, heteroaryl of 5 ring atoms having a single hetero-atom selected from oxygen, sulphur and nitrogen atoms and heteroaryl of 6 ring atoms having one nitrogen atom; and
R$^2$ and R$^3$ each stand for methyl;
or a pharmaceutically-acceptable acid-addition salt thereof.

2. A compound according to claim 1 wherein R° is a radical selected from the group consisting of methyl, n-butyl, methoxy and ethoxy radicals.

3. A compound according to claim 1 wherein R$^1$ is a radical selected from the group consisting of n-propyl, isopropyl, n-butyl, cyclo-propyl, phenyl, fluorophenyl, chlorophenyl, bromophenyl, methylphenyl, methoxyphenyl and trifluoromethylphenyl radicals.

4. A compound according to claim 1 wherein A represents a radical selected from the group consisting of 1,2-ethylene, 1,2-propylene, 2,3-propylene and 1,1-dimethyl-1,2-ethylene radicals.

5. A pharmaceutical composition for use as a 5-hydroxytryptamine antagonist, comprising an effective amount of a compound of the formula I, wherein A, Q, R°, R$^1$, R$^2$ and R$^3$ have the meanings stated in claim 1, or a pharmaceutically-acceptable acid-addition salt thereof, and an inert pharmaceutically- acceptable diluent or carrier.

6. A compound according to claim 1 wherein R$^1$ is a furyl, thienyl or pyridyl radical.

7. In a method of treatment which requires the use of a 5-hydroxytryptamine antagonist, the improvement which comprises using, as the antagonist, an effective amount of a compound according to claim 1.

* * * * *